United States Patent
Hermescec et al.

(10) Patent No.: US 6,596,908 B1
(45) Date of Patent: Jul. 22, 2003

(54) PROCESS FOR THE RECOVERY OF LOW MOLECULAR WEIGHT PHENOLS, FURFURAL, FURFURYL ALCOHOL AND/OR CELLULOSE OR CELLULOSE-RICH RESIDUES

(75) Inventors: Branko Hermescec, Creswick (AU); David Arthur Edward Butt, Ballarat (AU)

(73) Assignee: The University of Melbourne (AU)

( * ) Notice: Subject to any disclaimer, the term of this patent is extended or adjusted under 35 U.S.C. 154(b) by 0 days.

(21) Appl. No.: 09/856,865
(22) PCT Filed: Nov. 24, 1999
(86) PCT No.: PCT/AU99/01045
§ 371 (c)(1),
(2), (4) Date: Oct. 1, 2001
(87) PCT Pub. No.: WO00/31213
PCT Pub. Date: Jun. 2, 2000

(30) Foreign Application Priority Data
Nov. 24, 1998 (AU) .............................................. PP 7290

(51) Int. Cl.⁷ .......................... C07C 37/68; C08H 5/02; D21C 11/06; D21C 3/20
(52) U.S. Cl. ....................... 568/749; 568/761; 527/400; 162/47; 162/71; 162/77
(58) Field of Search ................. 568/749, 761; 162/47, 71, 77; 527/400

(56) References Cited

U.S. PATENT DOCUMENTS

| | | |
|---|---|---|
| 3,298,928 A | 1/1967 | Esterer |
| 4,322,222 A | 3/1982 | Sass |
| 4,511,433 A * | 4/1985 | Tournier et al. |
| 4,568,362 A | 2/1986 | Deglise et al. |
| 4,592,762 A | 6/1986 | Babu et al. |
| 4,968,325 A | 11/1990 | Black et al. |
| 5,223,601 A * | 6/1993 | Chum et al. |
| 5,395,455 A | 3/1995 | Scott et al. |
| 5,807,952 A | 9/1998 | Agblevor |

FOREIGN PATENT DOCUMENTS

| | | |
|---|---|---|
| EP | 0036 371 | 9/1981 |
| WO | WO 88/00935 | 2/1988 |
| WO | WO 89/05847 | 6/1989 |

* cited by examiner

Primary Examiner—Johann Richter
Assistant Examiner—Sikarl A. Witherspoon
(74) Attorney, Agent, or Firm—Knobbe, Martens, Olson & Bear, LLP

(57) ABSTRACT

A process for the recovery of furfural, furfuryl alcohol, low molecular weight phenols and/or cellulose or a cellulose-rich material from a lignocellulosic material comprising: feeding a carrier gas into a reaction chamber to facilitate a fluidised bed effect and to carry reaction products and residues away from the reactor via entrainment; introducing a feedstock comprising particulate lignocellulosic material of a predetermined particle size into the reaction chamber; degrading the feedstock in the reaction chamber under an oxygen-containing atmosphere at a temperature of from 250° C. to 320° C.; and quenching the degraded feedstock and carrier gas to deposit solid residue entrained in the carrier gas and to condense a liquid product.

14 Claims, 3 Drawing Sheets

Figure 1A:
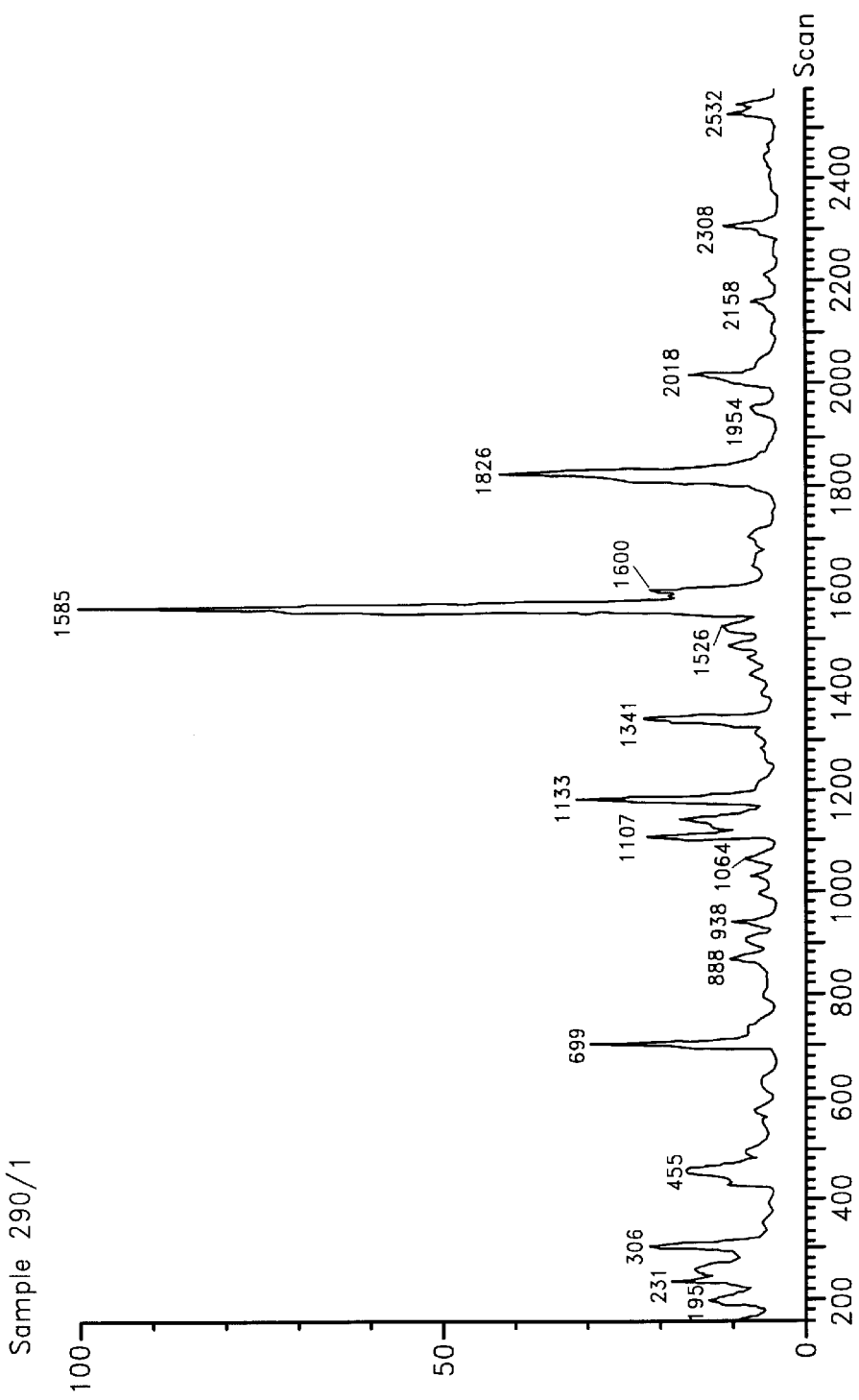

PROCESS FOR THE RECOVERY OF LOW MOLECULAR WEIGHT PHENOLS, FURFURAL, FURFURYL ALCOHOL AND/OR CELLULOSE OR CELLULOSE-RICH RESIDUES

This is the U.S. national phase under 36 U.S.C. §371 of International Application PCT/AU99/01045, filed Nov. 24, 1999.

The present invention relates to a process for the recovery of low molecular weight phenols, furfural and furfuryl alcohol and/or cellulose or cellulose-rich residues from a lignocellulosic biomass such as for example, hard or soft woods or other plant matter. In particular, the invention relates to a process for the pyrolysis-like degradation of lignocellulosic material to recover a high yield of low molecular weight phenols, furfural and furfuryl alcohol and/or cellulose or cellulose-rich residue.

Pyrolysis is a known process involving the thermal degradation of a biomass in the absence of oxygen. The process yields three product phases; a solid residue (char), pyroligneous liquor and low BTU gases. The relative yield of each phase depends on process parameters including reaction temperature, feedstock type and particle size, heat exchange method, equipment design and specification and product collection methods.

A number of methods are known for the pyrolysis of a biomass. These include batch type, ablative, vacuum, spinning disk and fluidised bed or flash pyrolysis. The main difference between these methods is the rate of heat transfer and the continuity of the process with respect to sample processing.

Hemi-celluloses are polymers of 5 carbon sugars and constitute a major component of wood. Under pyrolytic conditions at temperatures lower than that for lignin, hemi-celluloses degrades into furfural, furfuryl alcohol and furans. Wood contains 10–15% of hemicellulose.

Lignin is a major component of woody material. It is a complex, high molecular weight poly phenyl propane polymer with repeating units consisting of the species guaiacol and syringol. The basic function of lignin in wood is to bind the wood cells together.

Lignin accounts for 17–40% of total wood mass. It is known that the pyrolysis of lignin yields low molecular weight phenols, in particular guaiacol and its para alkyl substituted derivatives. More recent research has demonstrated that very rapid pyrolysis of lignocellulosic material yields higher quantities of pyrolysis oil, as well as increased concentrations of phenols in the pyrolysis oil, compared with traditional batch-type techniques. The rapid pyrolysis of lignocellulosic material, combined with rapid removal of the pyrolysis products from the heat source, facilitates the production of primary pyrolysis products as secondary pyrolysis is prevented.

In practice, rapid pyrolysis is achieved via the fluidised bed system. In this system, aluminosilicate sand contained within a cylindrical reactor is heated to the pyrolysis temperature. A gas is then passed through the sand bed. The flow of gas imparts fluid like properties to the sand bed. This system is referred to as a fluidised bed reactor. Feedstock may be introduced into the fluidised bed on a separate stream of gas. Upon contact with the hot sand bed, the feedstock is pyrolysed virtually instantaneously. The movement of gas through the system transports the pyrolysis products away from the hot sand bed to various product collection systems.

At temperatures in excess of 800° C., the gas phase is the dominant pyrolysis product. Such a regime has been used to produce low BTU gases for energy production. At temperatures between 600 and 800° C. char is the major product. This material may be used for iron ore processing and as a solid fuel. Pyrolysis oil is the major product at temperatures between 350 and 600° C. and because of this most research on pyrolysis oil has been focused in this temperature region. Under conventional fast pyrolysis conditions, very little occurs below 350° C.

Oils produced by the fast pyrolysis of lignocellulosic material between 350 and 600° C. are thermally and chemically unstable and contain a large, disparate range of compounds that have proven to be very difficult to resolve. Attempts have been made to utilise these oils as a fuel for energy production. However, little success has been achieved.

There has been considerable research conducted on the fast pyrolysis of lignocellulosic material with the aim of producing phenols for adhesive purposes. At present this research has not yielded a satisfactory process. This is due to thermal and chemical instability of the product, extreme complexity of the product, inability to scale up the process, expense of the process, and instability of the process with respect to hours of continuous run.

According to one aspect of the invention, there is provided a process for the recovery of furfural and furfuryl alcohol from a lignocellulosic material comprising:
 feeding a carrier gas into a reaction chamber to facilitate a fluidised bed effect and to carry reaction products and residues away from the reactor via entrainment;
 introducing a feedstock comprising particulate lignocellulosic material of a predetermined particle size into the reaction chamber;
 degrading the feedstock in the reaction chamber under an oxygen-containing atmosphere at a temperature of from 250° C. to 320° C.; and
 quenching the degraded feedstock and carrier gas to deposit solid residues entrained in the carrier gas and to condense a liquid product comprising furfural and furfuryl alcohol.

According to another aspect of the invention there is provided a process for the recovery of low molecular weight phenols from a lignocellulosic material comprising:
 feeding a carrier gas into a reaction chamber to facilitate a fluidised bed effect and to carry reaction products and residues away from the reactor via entrainment;
 introducing a feedstock comprising particulate lignocellulosic material of a predetermined particle size into the reaction chamber;
 degrading the feedstock in the reaction chamber under an oxygen-containing atmosphere at a temperature of from 250° C. to 320° C.; and
 quenching the degraded feedstock,and carrier gas to deposit solid residues entrained in the carrier gas and to condense a liquid product comprising a phenol-rich oil.

There is also provided furfural and furfuryl alcohol and low molecular weight phenols when recovered by a process as described in the immediately preceding two paragraphs respectively.

According to a further aspect of the invention there is provided a process for the recovery of cellulose or a cellulose-rich material from a lignocellulosic material comprising:
 feeding a carrier gas into a reaction chamber to facilitate a fluidised bed effect and to carry reaction products and residues away from the reactor via entrainment;
 introducing a feedstock comprising particulate lignocellulosic material of a predetermined particle size into the reaction chamber;

degrading the feedstock in the reaction chamber under an oxygen-containing atmosphere at a temperature of from 250° C. to 320° C.; and quenching the degraded feedstock and carrier gas to deposit solid residues comprising cellulose or cellulose-rich material entrained in the carrier gas.

There is further provided cellulose or cellulose-rich material recovered by a process as described in the immediately preceding paragraph.

The classical definition of pyrolysis does not allow for the presence of oxygen in the reaction atmosphere because, at normal pyrolysis temperatures, combustion would occur. However, in the present invention it has been found that the presence of oxygen in the reaction atmosphere promotes the degradation of lignin under the conditions of the invention to recover phenols as a degradation product. Further, it has been found that under these conditions the cellulose component remains substantially intact. In one embodiment, the degradation is carried out under an oxygen-enriched atmosphere.

When it is desired to produce an oil, conventional fast pyrolysis is generally conducted at a temperature of from 350 to 500° C. Under such temperatures, the rate of cellulose and lignin pyrolysis is high. As such, the resultant oil contains degradation products from both components, resulting in a complex, thermally and chemically unstable product which has practically no useful application. According to the present invention, where temperatures of pyrolysis range from 250 to 320° C., the rate of cellulose pyrolysis is very low whereas the rate of lignin pyrolysis is much higher, though still quite low compared with that at higher temperatures. The presence of oxygen in the process of the invention, however, promotes lignin degradation, thus yielding a phenol-rich oil. Therefore, due to the lower temperatures employed in the process of the present invention, compared with conventional fast pyrolysis processes, the oil recovered contains very little of the pyrolysis products of cellulose and is, therefore, much simpler and more stable compared to normal pyrolysis oils. Furthermore, the oils produced in accordance with the present invention advantageously contain no tar. In a preferred embodiment, the degradation of the feedstock is conducted at a temperature of from about 290° C. to 310° C. when it is desired to maximise low molecular weight phenol production. When it is desired to maximise furfural and furfuryl alcohol degradation is preferably conducted at a temperature of from about 250° C. to 270° C.

Conventionally, the particle size of the lignocellulosic feedstock is 500 $\mu$m or more. The particle size of feedstock used in accordance with the present invention, which is selected generally in consideration of operating parameters for a particular application is preferably less than 1 mm, but is generally considerably smaller than that conventionally employed. The reasons for the use of such small particles is threefold.

Firstly, the retention time for feedstock in the reaction chamber is very short, being only slightly longer than that used in conventional pyrolysis processes. As such, the time available for heat transfer is comparable to that in conventional processes. However, due to the lower temperatures used according to the invention, the heat available for transfer is considerably less. Therefore, the extent to which pyrolysis occurs will be less if the invention is compared to conventional fast pyrolysis processes using conventional particle sizes. In order to overcome this, a much smaller particle size is used so as to enable a higher rate of pyrolysis due to the lower energy requirement compared with that for larger particles.

Secondly, the mass of the particles used in the invention is much less than that normally used. This means that the velocity of the carrier gas required to entrain the partially pyrolysed particles and carry them out of the reactor to a cooler environment (and thus preventing secondary pyrolysis/charring) is comparatively low. This also permits a sufficient residence time for the particle in the fluid bed. The entrained residues are captured, yielding a material that is high in cellulose and low in lignin.

Thirdly, for small particles, the reaction atmosphere is more likely to be able to penetrate completely into the particle, thus homogenising the atmospheric effect. For larger particles this is less likely to occur.

In a preferred embodiment, the lignocellulosic material has a particle size of from 100 to 250 $\mu$m. It will be recognised that optimal particle sizes may be determinable depending on the other parameters used in a particular application of the invention.

Production of guaiacol (2-methoxy phenol), the dominant phenol in distillate samples recovered using the invention, has been found to be greatest when particle size is small (less than 500 $\mu$m) in an atmosphere of air and at a temperature of approximately 300° C.

Since the degradation reaction is conducted just below the activation temperature for cellulose, the solid residues mainly contain unpyrolysed cellulose. When all reactions parameters are at the optimum, the separation of volatile products of pyrolysed lignin and extractives from the unreacted residue is advantageously quite complete.

The reaction chamber comprises a fluidised bed containing sand particles. Unlike conventional applications, however, where sand particle size in the bed is generally from 250 to 1000 $\mu$m, the fluidised bed used in the process of the invention preferably contains sand of a particle size from about 100 to about 500 $\mu$m.

The small particle size of the lignocellulosic feedstock permits a lower carrier gas feed rate than is conventionally used. Preferably, the feedstock is fed into the reaction chamber in a stream of carrier gas. The flow rate of the carrier gas is less than that conventionally used (which are generally in the order of 6 liter/minute or more), and is expected to vary according to the cross sectional area of the reactor. For example, the flow rate may be from about 4 to about 6 liters/minute.

In order to immobilise the solid residue and separate it from the liquid product a new system has been developed. The system comprises an inner section which facilitates the deposition and collection of solid residues entrained in the carrier gas stream. The temperature in this section is preferably less than 250° C. As such, the solid residue will not undergo further pyrolysis. The carrier gases then pass to the next stage of the system. This is a quenching process. The carrier gas is advantageously bubbled through a solvent, causing most of the associated pyroligneous vapour to be condensed. The solvent is preferably kept at a temperature below 0° C. After the carrier gas has passed through the quenching fluid it then enters an electrostatic precipitator where any material not condensed in the quenching system is immobilised.

It has been found that the solid residue contained in the inner vessel of the quenching system is generally in good condition. That is, it contains no char. Further, the residue has been found to be significantly de-lignified and contains a high proportion of cellulose.

It should be noted that the above description of the setup of the invention is one which has been devised for bench top operation and may require modification or variation in scale-up to industrial application. As such, this should not be construed as limiting on the invention in any way.

Further, it has been found that the process of the invention which advantageously provides a multi-stage degradation, more particularly a three stage degradation, of specific constituents of wood in turn results in products having desirous and improved characteristics compared with products obtained by prior art processes.

EXPERIMENTAL RESULTS FROM THE INVENTION

The following examples of experimental results are provided for exemplification only and should not be construed as limiting on the invention in any way.

Figure 1B:
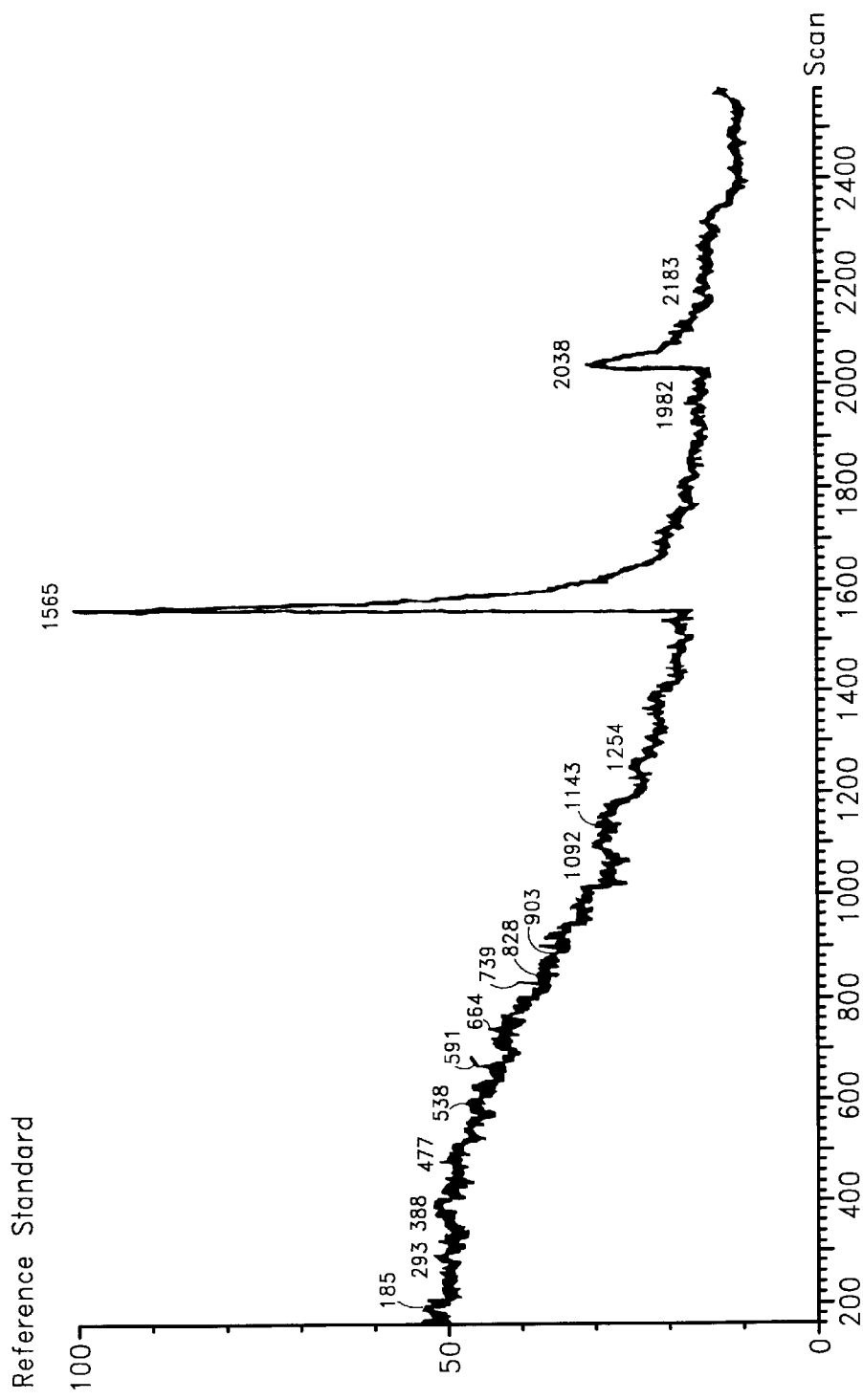

Experimental results from the invention indicate that 2-Methoxy Phenol, or Guaiacol, is, by far, the most abundant phenol produced from soft wood material. It also possesses the lowest molecular mass and the simplest structure. A reference standard of guaiacol was analysed to validate its identification in the samples. Mass spectrum and retention time comparisons were used to do this. FIGS. 1A and 1B display the chromatographic peaks of guaiacol in a sample and in the reference standard respectively.

Figure 2:
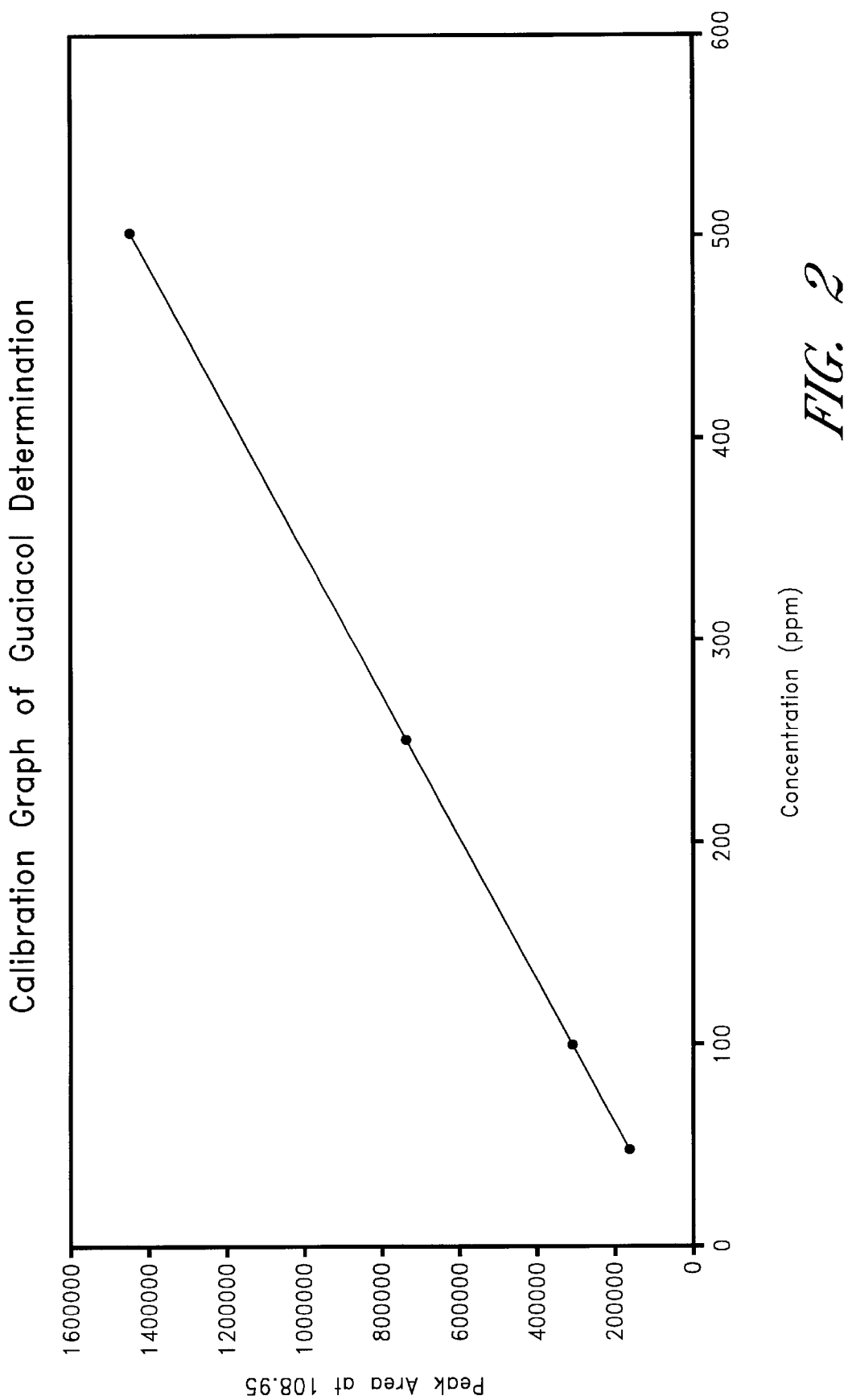

A calibration graph was generated by testing a series of guaiacol standards of known concentration. The calibration graph is displayed in FIG. 2.

The results of the quantification of guaiacol in the samples are displayed in Tables 1–5.

TABLE 1

Quantitative results for guaiacol in series 1 samples (Sample size < 1 mm).

| Sample | Dilution factor | Peak area (M/Z = 108.95) | Concentration of Guaiacol in test samples (ppm) | Concentration of Guaiacol in raw samples (ppm) |
|---|---|---|---|---|
| S170_1L | 0 | 0 | 0 | 0 |
| S210_1L | 0 | 0 | 0 | 0 |
| S250_1L | 0 | 0 | 0 | 0 |
| S270_1L | 0 | 656,815 | 220 | 2,200 |
| S290_1L | 20 | 1,129,878 | 385 | 77,000 |

TABLE 2

Quantitative results for guaiacol in series 2 Samples (Sample size between 1–3 mm).

| Sample | Dilution factor | Peak area (M/Z = 108.95) | Concentration of Guaiacol in test samples (ppm) | Concentration of Guaiacol in raw samples (ppm) |
|---|---|---|---|---|
| S170_2L | 0 | 0 | 0 | 0 |
| S230_2L | 0 | 57,263 | 11.9 | 118 |
| S250_2L | 0 | 442,302 | 146 | 1,460 |
| S270_2L | 0 | 1,718,182 | 589 | 5,890 |
| S290_2L | 0 | 793,950 | 268 | 2,680 |

TABLE 3

Quantitative results for guaiacol in series 3 samples (Sample size between 3 mm).

| Sample | Dilution factor | Peak area (M/Z = 108.95) | Concentration of Guaiacol in test samples (ppm) | Concentration of Guaiacol in raw samples (ppm) |
|---|---|---|---|---|
| S170_3L | 0 | 0 | 0 | 0 |
| S210_3L | 0 | 0 | 0 | 0 |
| S230_3L | 0 | 1,824,794 | 626 | 6,260 |
| S250_3L | 0 | 371,966 | 121 | 1,210 |
| S270_3L | 0 | 264,519 | 84 | 840 |
| S290_3L | 0 | 1,063,551 | 362 | 3,620 |

TABLE 4

Quantitative results for guaiacol in series 4 samples (Sample size > 6 mm).

| Sample | Dilution factor | Peak area (M/Z = 108.95) | Concentration of Guaiacol in test samples (ppm) | Concentration of Guaiacol in raw samples (ppm) |
|---|---|---|---|---|
| S170_4L | 0 | 0 | 0 | 0 |
| S210_4L | 0 | 0 | 0 | 0 |
| S230_4L | 0 | 0 | 0 | 0 |
| 5250_4L | 0 | 38,366 | 5.3 | 53 |
| S290_4L | 0 | 517,441 | 172 | 1,720 |

TABLE 5

Quantitative results for guaiacol produced under nitrogen atmosphere.

| Sample | Dilution factor | Peak area (M/Z = 108.95) | Concentration of Guaiacol in test samples (ppm) | Concentration of Guaiacol in raw samples (ppm) |
|---|---|---|---|---|
| S170_NAL | 0 | 0 | 0 | 0 |
| S210_NAL | 0 | 0 | 0 | 0 |
| S230_NAL | 0 | 0 | 0 | 0 |
| S250_NAL | 0 | 0 | 0 | 0 |
| S270_NAL | 0 | 0 | 0 | 0 |
| S290_NAL | 0 | 1,567,601 | 537 | 5,370 |
| S310_NAL | 0 | 1,678,345 | 575 | 5,750 |
| S330_NAL | 0 | 1,838,437 | 631 | 6,310 |

The tables above show that the yield of guaiacol in a pyrolysis oil is inversely related to the sample particle size and that the presence of oxygen considerably increases the yield of this phenol.

Phenols are a group of chemicals that constitute one of the most essential raw materials for further synthesis and processes. The world demand for phenols stands at 10–12 million tons per annum at the market value of 20–30 billion dollars. There is a shortfall of these products of about 2 million tons per year. Additional production capacities to be build in the countries of South East Asia, Europe and the Americas are in the planning stage and will be build by the year of 2000.

End uses for phenols include, for example, composite materials (Bakelite), medicines, food flavourings, explosives, waterproof adhesives, and plastics.

Guaiacol is quite difficult to synthesise, hence it market price is high, above that for resorcinaol (5000–6000 dollars per ton). It is believed that the production cost of quaiacol produced by this invention will be much lower than that of the conventional production method. It is also believed that the method of the invention will be more valuable in future as it offers phenolic product derived from renewable resource and the likelihood of carbon remaining bound for extended time is high.

Cellulose is one of the most diverse commodities without which a modern society could not function. Paper and paper related products are most obvious products. Additionally, cellulose is used for a wide range of products and processes including viscose, rayon and composite materials. Australia uses some three billion dollars worth of cellulosic products, which is approximately 1% of the world consumption of cellulosic materials. Two thirds of Australian needs in cellulosic materials are imported.

Conventionally, cellulose is produced by one of few methods of chemical pulping of wood. It is the process of de-lignification, where lignin the binding agent is chemically degraded and washed out of the cellulose residue. Some processes utilise the black liquor residues for energy generation and chemicals recovery. However, the organic material contained in the black liquor is largely unused. Market value of cellulose is about 1000–1200 dollars per ton. Conventional pulping methods require woodchips of certain geometry, unobtainable from unhomogeneous wood waste.

The cellulose derived by the process of this invention is believed to be suitable for the purposes of reconstituted cellulose products and it is equivalent to the cellulose derived by the pulping method. The main advantage of the cellulose derived by this invention is lower production cost and raw material specifications. Processing of biomass by this invention offers almost 100% utilisation. The process is energy neutral, generating sufficient quantities of low BTU gas to power itself.

Throughout this specification and the claims which follow, unless the context requires otherwise, the word "comprise", and variations such as "comprises" and "comprising", will be understood to imply the inclusion of a stated integer or group of integers or steps but not the exclusion of any other integer or group of integers or steps.

Those skilled in the art will appreciate that the invention described herein is susceptible to variations and modifications other than those specifically described. It is to be understood that the invention includes all such variations and modifications which fall within its spirit and scope. The invention also includes all the steps, features, compositions and compounds referred to or indicated in this specification, individually or collectively, and any and all combinations of any two or more of said steps or features.

What is claimed is:

1. A process for the recovery of a useful product from the lignocellulosic material comprising:

feeding a carrier gas into a reaction chamber to facilitate a fluidised bed effect and to carry reaction products and residues away from the reactor via entrainment;

introducing a feedstock comprising particulate lignocellulosic material of a predetermined particle size into the reaction chamber;

degrading the feedstock in the reaction chamber under an oxygen-containing atmosphere at a temperature of from 250° C. to 320° C.; and quenching the degraded feedstock and carrier gas to deposit solid residues entrained in the carrier gas and to condense at least one liquid product.

2. The process according to claim 1, wherein said useful product is said liquid product, wherein said liquid product comprises a phenol-rich oil.

3. The process according to claim 1, wherein said useful product is a solid residue, wherein said residue comprises cellulose or cellulose-rich material.

4. The process according to claim 1, wherein the degradation is carried out under an oxygen-enriched atmosphere or an air atmosphere.

5. The process according to claim 1, wherein the degradation of the feedstock is conducted at a temperature of from about 250° C. to 270° C.

6. The process according to claim 2, wherein the degradation of the feedstock is conducted at a temperature of from about 250° C. to 270° C.

7. The process according to claim 1, wherein the lignocellulosic material has a particle size of less than 1 mm.

8. The process according to claim 1, wherein the lignocellulosic material has a particle size of from 100 to 250 $\mu$m.

9. The process according to claim 1, wherein the reaction chamber comprises a fluidised bed containing sand particles.

10. The process according to claim 9, wherein the fluidised bed contains sand particles having a particle size of form about 100 to about 500 $\mu$m.

11. The process according to claim 1, wherein immobilisation of the solid residue and separation of the solid residue from the liquid product is conducted in a system comprising an inner section which facilitates the deposition and collection of solid residues entrained in the carrier gas stream, a quenching section wherein pyroligneous vapour is condensed and an immobilisation section including an electrostatic precipitator where any material not condensed in the quenching section is immobilised.

12. The process according to claim 11, wherein the temperature in the inner section is less than 250° C.

13. The process according to claim 11, wherein in said quenching section the carrier gas is bubbled through a solvent, said solvent being at a temperature below 0° C.

14. The process according to claim 1, wherein said useful product is said liquid product, wherein said liquid product is furfural and furfuryl alcohol.

* * * * *

UNITED STATES PATENT AND TRADEMARK OFFICE
CERTIFICATE OF CORRECTION

PATENT NO. : 6,596,908 B1
DATED : July 22, 2003
INVENTOR(S) : Branko Hermescec et al.

It is certified that error appears in the above-identified patent and that said Letters Patent is hereby corrected as shown below:

Column 7,
Line 52, after "product" delete "from the lignocellulosic" and insert therefor -- selected from the group consisting of a phenol-rich oil, cellulose or cellulose-rich material, furfural and furfuryl alcohol, from a lignocellulosic --

Signed and Sealed this

Twenty-fifth Day of May, 2004

JON W. DUDAS
*Acting Director of the United States Patent and Trademark Office*